United States Patent [19]

Sampson et al.

[11] Patent Number: 4,573,976

[45] Date of Patent: Mar. 4, 1986

[54] SHIELDED NEEDLE

[75] Inventors: Norma A. Sampson, Fullerton; Earl W. Sampson, Ontario, both of Calif.

[73] Assignee: Dolores A. Smith, Fullerton, Calif.; a part interest

[21] Appl. No.: 613,460

[22] Filed: May 24, 1984

[51] Int. Cl.⁴ .............................................. A61M 5/00
[52] U.S. Cl. ...................................... 604/198; 604/263
[58] Field of Search ................ 604/198, 197, 192, 187, 604/263, 171

[56] References Cited

U.S. PATENT DOCUMENTS

| | | | |
|---|---|---|---|
| 2,925,083 | 2/1960 | Craig | 604/197 |
| 3,780,734 | 12/1973 | Wolff | 604/197 |
| 3,890,971 | 6/1975 | Leeson et al. | 604/197 X |
| 4,425,120 | 1/1984 | Sampson et al. | 604/198 |

Primary Examiner—Stephen C. Pellegrino
Attorney, Agent, or Firm—Weissenberger and Peterson

[57] ABSTRACT

An apparatus for injecting a substance into a human or animal comprising a body adapted to have the substance to be injected pass therethrough, a needle mounted on the body and a needle guard mounted on the body between an extended position in which the guard obstructs access to the point of the needle and a retracted position in which the guard does not materially obstruct access to the point of the needle. The guard is releasably retained in the retracted position, and interlocking members on the body and the guard are responsive to generally axial movement of the guard to the extended position for interlocking to substantially prevent movement of the guard back toward the retracted position.

14 Claims, 6 Drawing Figures

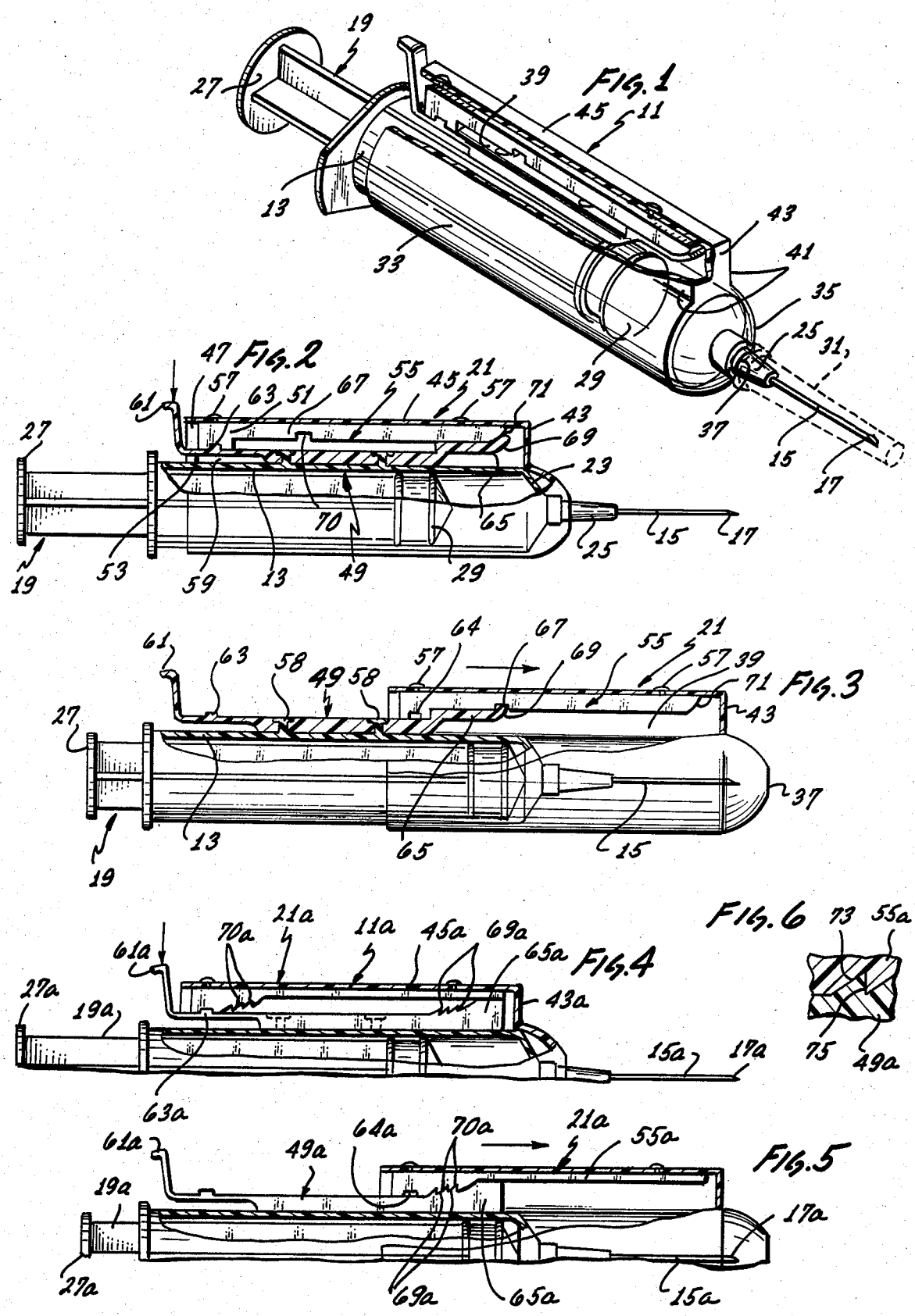

SHIELDED NEEDLE

BACKGROUND OF THE INVENTION

Various apparatuses, such as hypodermic syringes and intravenous needles, are utilized for injecting a substance into humans and animals. Apparatuses of this type typically comprise a body adapted to have the substance to be injected passed therethrough and a needle mounted on the body. The substance to be injected can be forced through the needle in various ways, such as by a plunger carried by the body or by external means, such as a pump or gravitational flow.

Apparatuses of this type are typically disposable and are discarded after use. One problem presented by the disposal of these apparatuses is in shielding the sharp end of the needle so that those handling it will not be stuck. This is particularly important because, following the injection, the needle may be contaminated and spread blood-transmitted diseases, such as hepatitis or AIDS.

Our U.S. Pat. No. 4,425,120 discloses a shielded hypodermic syringe in which a guard can be slid along the body from a retracted position to an extended position. In the extended position, the guard covers the point of the needle so as to protect those handling it from being stuck by the needle point. The guard is normally releasably retained in a retracted position. To actuate the guard, the guard is first rotated in one direction to release it, then advanced axially to the extended position and finally rotated to positively lock the guard in the extended position. Although the patented construction is very satisfactory, it is desired to provide for the locking and releasing of the guard without the need to employ rotational movement of the guard.

SUMMARY OF THE INVENTION

This invention eliminates the need for rotational movement of the guard to release the guard for movement toward the extended position and to lock the guard in the extended position. Although some rotational movement of the guard can be used, if desired, only the axial movement of the guard along the body is needed.

With this invention, interlocking means is provided on the body and the guard, and the interlocking means is responsive to movement of the guard on the body generally axially to the extended position for interlocking to substantially prevent movement of the guard back toward the retracted position. The guard can be released from the retracted position by moving an interlocking member generally radially of the body. Thus, to actuate the guard, it is only necessary to move the interlocking member radially to release the guard and advance the guard axially to the extended position. When the guard reaches the extended position, it is automatically retained therein without the need for rotating the guard on the body.

The interlocking means for locking the guard in the extended position preferably includes interlocking members on the guard and the body. At least a portion of one, or both, of the interlocking members is resiliently deflectable to allow the interlocking members to interlock. The interlocking members, when interlocked, are substantially nonseparable to prevent movement of the guard from the extended position toward the retracted position. In other words, when the interlocking members are interlocked, the guard cannot be returned to the retracted position without applying forces sufficient to permanently deform or break the interlocking members. In this way, the guard is positively locked in the extended position and not merely releasably retained in the extended position.

The means for releasably retaining the guard in the retracted position preferably includes interlocking members on the body and the guard and means for mounting at least one of the interlocking members for movement generally radially of the body to release the guard for movement toward the extended position.

In a preferred construction, wall means defines an elongated channel on one of the body and the guard, and a rib is provided on the other of the body and the guard. The rib is receivable in the channel. This construction is useful for a multiplicity of purposes. For example, although various different means can be used to guide the axial movement of the guard along the body, the cooperation between the rib and the channel can advantageously accomplish this purpose. In addition, portions of the rib may be used to define all, or portions of, some of the interlocking members. The other interlocking members can be carried by, or formed on, the channel.

The invention, together with additional features and advantages thereof, may best be understood by reference to the following description taken in connection with the accompanying illustrative drawing.

BRIEF DESCRIPTION OF THE DRAWING

FIG. 1 is an isometric view partially in section of one form of hypodermic syringe constructed in accordance with the teachings of this invention.

FIG. 2 is a side elevational view partially in section of the syringe with the guard in the retracted position.

FIG. 3 is an elevational view partially in section similar to FIG. 2 with the guard in the extended position.

FIG. 4 is a fragmentary, side elevational view partially in section of a second embodiment of hypodermic syringe of this invention with the guard in the retracted position.

FIG. 5 is a fragmentary, side elevational view partially in section similar to FIG. 4 with the guard in the extended position.

FIG. 6 is a fragmentary sectional view of the interlocking sawtooth projections.

DESCRIPTION OF THE PREFERRED EMBODIMENTS

Although this invention is applicable to a variety of injection apparatuses, FIGS. 1–3 disclose an apparatus in the form of a hypodermic syringe 11. The syringe 11 generally comprises a body or barrel 13 adapted to contain a substance to be injected, a hypodermic needle 15 terminating in a point 17 and having an axial passage extending therethrough, a plunger 19 and a guard 21. The plunger 19 is mounted for axial sliding movement within the body 13 for forcing the substance from the body and through the passage of the needle 15 in a conventional manner.

The body 13, the needle 15 and the plunger 19 may be of conventional construction. In the embodiment illustrated, the body 13 is in the form of a hollow plastic cylinder having an end wall 23 (FIG. 2) to which the needle 15 is attached in a conventional manner by a needle mounting member 25. The needle 15 is coaxial with the body 13. The plunger 19 projects out of one end of the body 13 to define a flat outer end 27 which facilitates manual movement of the plunger within the barrel. The plunger 19 has a piston 29 at its inner end to expel the substance from the barrel through the passage of the needle 15. The syringe 11 may also include a conventional shield 31 in the form of an elongated hollow cylinder which is frictionally retained on the needle mounting member 25 (FIG. 1).

The guard 21 includes a generally cylindrical wall 33 having one end open to receive the body 13 and its opposite end partially closed by an end wall 35. The end wall 35 has an opening 37 through which the needle 15 can project in the retracted position shown in FIGS. 1 and 2. The guard 21 also includes wall means defining a channel 39 which opens radially inwardly. Although the wall means can be of various different constructions, in the embodiment illustrated, it includes spaced parallel side walls 41, an end wall 43 closing one end of the channel 39 and a wall 45 closing the radial outer region of the channel 39. The end of the channel 39 opposite the end wall 43 has an opening 47.

As shown in FIGS. 1–3, the channel 39 extends axially of the body 13 and the guard 21, and it is elongated in the axial direction. An elongated rib 49 is mounted on the body 13 and extends axially along the outer surface of the body. Although the guard 21 can be mounted for axial movement on the body 13 in various different ways, in the embodiment illustrated, the rib 49 is received within the channel 39 with a modest clearance to mount the guard for axial movement along the body.

Means is provided for releasably retaining the guard 21 in the retracted position shown in FIG. 2 in which the guard does not obstruct access to the point 17 of the needle 15. Although this can be accomplished in different ways, it is preferred to utilize an interlocking member 51 carried by the guard 21 and an interlocking member 53 carried by the body 13. In the embodiment illustrated, the interlocking member 51 is an end portion of an elongated member 55 which extends axially within the channel 39. Although various different constructions are possible, in the embodiment illustrated, the elongated member 55 is a separate member which is attached by suitable fasteners 57 to the wall 45. The interlocking member 53 can advantageously be an end portion of the rib 49. The rib 49 may be molded integrally with the body 13 or molded separately and suitably attached thereto as by fasteners 58. The rib 49 has an undercut 59 beneath the interlocking member 53 to enable the interlocking member to be resiliently deflected radially inwardly from the position shown in FIG. 2. An end portion of the interlocking member 53 projects out through the opening 47 to define a tab 61 which can be manually depressed radially inwardly.

To retain the guard 21 in the retracted position, the interlocking member 53 has a projection 63 which is received within a mating groove 64 of the interlocking member 51. Of course, the positions of the projection 63 and the associated groove can be reversed, if desired. By depressing the tab 61 radially inwardly, the projection 63 is removed from the mating groove 64 to permit the guard 21 to be advanced axially from the retracted position to the extended position.

Interlocking means positively locks the guard 21 in the extended position. In the embodiment of FIGS. 1–3, such interlocking means comprises a resilient interlocking member 65 defined by one end portion of the rib 49 and an interlocking member 67 defined by a portion of the elongated member 55. The interlocking member 65, which can be resiliently deflected radially inwardly, has a projection 69, and the interlocking member 67 has a corresponding groove 70 for lockingly receiving the projection 69. Of course, the projection 69 and groove 70 may be reversed on the interlocking members 65 and 67, if desired. The surfaces defining the projection 69 and its associated groove 70 are rigid surfaces, and the end walls of these surfaces are generally perpendicular to the axes of the body 13 and the guard 21. Accordingly, with the projection 69 received within its associated groove 70, the interlocking members are interlocked such that they are substantially nonseparable to prevent movement of the guard 21 from the extended position toward the retracted position. Moreover, the interlocking member 65 is housed by the guard 21 in the extended position so that inadvertent resilient movement of the interlocking member 65 radially inwardly is essentially impossible. Accordingly, the guard 21 can be positively locked in the extended position, and to return the guard to the retracted position, it would be necessary to apply sufficient force to break one or both of the interlocking members 65 and 67.

One end of the elongated member 55 forms a cam 71 (FIG. 2) which engages, or is in close proximity to, a correspondingly curved exterior surface of the interlocking member 65. In order to advance the guard 21 from the retracted position of FIG. 2 to the extended position of FIG. 3, it is necessary to apply sufficient axial force to the guard to enable the cam 71 to cam the interlocking member 65 radially inwardly.

In use of the syringe 11, the guard 21 is pulled from the needle mounting member 25, and the substance to be injected is drawn into the body 13 in the usual manner by retracting the plunger 19. The substance is then injected into the human or animal by depressing the plunger 19. Thereafter, the tab 61 is pushed radially inwardly to release the projection 63 from the groove 64, and the guard 21 is moved axially to the extended position of FIG. 3. In response solely to this axial movement, the projection 69 snaps into the groove 70 when the extended position is reached. In the extended position, the point 17 of the needle is completely housed within the guard 21 so that the point 17 is entirely within the guard.

The guard 21, and more particularly the wall means defining the channel 39, houses the elongated member 55, and in the retracted position, also houses the rib 49. Although the walls 43 and 45 can be eliminated, if desired, their presence is preferred in order to totally enclose the interlocking member 65 in the extended position.

FIGS. 4 and 5 show a second embodiment of hypodermic syringe 11a which is identical to the hypodermic syringe 11 in all respects not shown or described herein. Portions of the syringe 11a corresponding to portions of the syringe 11 are designated by corresponding reference numerals followed by the letter "a."

The only difference between the syringes 11 and 11a is in the construction of the rib 49a and the elongated member 55a. More specifically, the interlocking member 65a formed on the rib 49a is not deflectable radially inwardly. Rather, the interlocking member includes a plurality of sawtooth projections 69a which are somewhat resiliently deflectable in response to an axial force acting in the direction of movement of the guard 21a from the retracted position to the extended position.

The elongated member 55a does not have the cam 71, and the groove 70 is replaced by sawtooth projections 70a which are adapted to mate with the projections 69a. The projections 70a are deformable in response to an axial force acting in the direction of movement of the guard 21a from the retracted position to the extended position.

To release the guard 21a for movement from the retracted position to the extended position, the tab 61a is depressed to remove the projection 63a from the groove 64a. The guard 21a can then be manually moved axially to the extended position of FIG. 5. The sawtooth projections 69a and 70a can be forced together by virtue of the resilience of these teeth in the direction of movement of the guard 21a and because of inclined ramp surfaces 73 on the projections 69a and 70a. However, once the teeth are interlocked, retrograde movement of the guard 21a from the extended position to the retracted position is not possible without applying sufficient force to permanently deform or rupture these teeth. This is because the sawtooth projections 69a and 70a have flat confronting seating surfaces 75 which lie in a radial plane as shown in FIG. 6.

Although exemplary embodiments of the invention have been shown and described, many changes, modifications and substitutions may be made by one having ordinary skill in the art without necessarily dearting from the spirit and scope of this invention.

We claim:

1. An apparatus for injecting a substance into a human or an animal comprising:
   a body adapted to have the substance to be injected pass therethrough;
   means for mounting a needle on the body with the needle having a passage extending therethrough and terminating in a point whereby the substance can pass from the body to and through the passage of the needle;
   a removable shield covering said needle;
   a needle guard having open opposite ends movable on the body between an extending position in which the guard obstructs access to the point of the needle and a retracted position in which the guard does not materially obstruct access to the point of the needle and in which the needle and shield project through one of said open ends of said needle guard, said extended and retracted positions being axially spaced;
   means for releasably retaining the guard in the retracted position; and
   means on the body and the guard for resisting movement of the guard from the extended position back toward the retracted position.

2. An apparatus as defined in claim 1 wherein said interlocking means includes resisting members on the body and the guard, at least one of the interlocking members being resiliently deflectable to allow the interlocking members to interlock, said interlocking members when interlocked being substantially nonseparable to thereby prevent movement of the guard from the extended position toward the retracted position.

3. An apparatus as defined in claim 1 including wall means defining an elongated channel on one of said body and said guard and a rib on the other of said body and said guard receivable in said channel.

4. An apparatus as defined in claim 1 including an axially extending radially opening channel on said guard and an elongated axially extending rib on said body received in said channel to axially guide the shield between said positions thereof.

5. An apparatus as defined in claim 1 including radially inwardly and radially outwardly projecting members carried by said needle guard and said body, respectively, and engageable in said extended position to define said extended position.

6. An apparatus for injecting a substance into a human or an animal comprising:
   a body adapted to have the substance to be injected pass therethrough;
   means for mounting a needle on the body with the needle having a passage extending therethrough and terminating in a point whereby the substance can pass from the body to and through the passage of the needle;
   a needle guard movable on the body between an extended position in which the guard obstructs access to the point of the needle and a retracted position in which the guard does not materially obstruct access to the point of the needle, said extended and retracted positions being axially spaced;
   means for releasably retaining the guard in the retracted position;
   interlocking means on the body and the guard responsive to movement of the guard on the body generally axially to the extended position for interlocking to substantially prevent movement of the guard back toward the retracted position; and
   said retaining means including interlocking members on said body and said guard and means for mounting at least one of said interlocking members for movement generally radially of the body to release the guard for movement toward the extended position.

7. An apparatus as defined in claim 6 wherein said one interlocking member is on said body.

8. An apparatus for injecting a substance into a human or an animal comprising:
   a body adapted to have the substance to be injected pass therethrough;
   means for mounting a needle on the body with the needle having a passage extending therethrough and terminating in a point whereby the substance can pass from the body to and through the passage of the needle;
   a needle guard movable on the body between an extended position in which the guard obstructs access to the point of the needle and a retracted position in which the guard does not materially obstruct access to the point of the needle, said extended and retracted positions being axially spaced;
   means for releasably retaining the guard in the retracted position;
   interlocking means on the body and the guard responsive to movement of the guard on the body generally axially to the extended position for interlocking to substantially prevent movement of the guard back toward the retracted position;
   wall means defining an elongated channel on one of said body and said guard and a rib on the other of said body and said guard receivable in said channel; and
   said interlocking means including a deflectable portion of said rib and an interlocking member carried in the channel.

9. An apparatus for injecting a substance into a human or an animal comprising:

a body adapted to have the substance to be injected pass therethrough;

means for mounting a needle on the body with the needle having a passage extending therethrough and terminating in a point whereby the substance can pass from the body to and through the passage of the needle;

a needle guard movable on the body between an extended position in which the guard obstructs access to the point of the needle and a retracted position in which the guard does not materially obstruct access to the point of the needle, said extended and retracted positions being axially spaced;

means for releasably retaining the guard in the retracted position;

interlocking means on the body and the guard responsive to movement of the guard on the body generally axially to the extended position for interlocking to substantially prevent movement of the guard back toward the retracted position;

wall means defining an elongated channel on one of said body and said guard and a rib on the other of said body and said guard receivable in said channel; and said retaining means including a portion of said rib and an interlocking member carried by said channel.

10. An apparatus as defined in claim 9 wherein said portion of said rib is resiliently movable and projects out of said channel in said retracted position to define a tab which can be manually activated.

11. An apparatus for injecting a substance into a human or an animal comprising:

a body adapted to have the substance to be injected pass therethrough;

means for mounting a needle on the body with the needle having a passage extending therethrough and terminating in a point whereby the substance can pass from the body to and through the passage of the needle;

a needle guard movable on the body between an extended position in which the guard obstructs access to the point of the needle and a retracted position in which the guard does not materially obstruct access to the point of the needle, said extended and retracted positions being axially spaced;

means for releasably retaining the guard in the retracted position;

interlocking means on the body and the guard responsive to movement of the guard on the body generally axially to the extended position for interlocking to substantially prevent movement of the guard back toward the retracted position; and said interlocking means including a first interlocking member carried by said body and resiliently movable radially inwardly of the body and a second interlocking member carried by said guard, said first interlocking member being forceable radially inwardly and movably radially outwardly to interlock with the second interlocking member when the guard reaches said extended position, said first and second interlocking members having rigid surfaces which are engageable in said extended position.

12. An apparatus for injecting a substance into a human or an animal comprising:

a body adapted to have the substance to be injected pass therethrough;

means for mounting a needle on the body with the needle having a passage extending therethrough and terminating in a point whereby the substance can pass from the body to and through the passage of the needle;

a needle guard movable on the body between an extended position in which the guard obstructs access to the point of the needle and a retracted position in which the guard does not materially obstruct access to the point of the needle, said extended and retracted positions being axially spaced;

means for releasably retaining the guard in the retracted position;

interlocking means on the body and the guard responsive to movement of the guard on the body generally axially to the extended position for interlocking to substantially prevent movement of the guard back toward the retracted position; and said interlocking means including a plurality of interlocking teeth carried by said guard and said body for interlocking in the extended position.

13. An apparatus for injecting a substance into a human or an animal comprising:

a body adapted to have the substance to be injected pass therethrough;

means for mounting a needle on the body with the needle having a passage extending therethrough and terminating in a point whereby the substance can pass from the body to and through the passage of the needle;

a needle guard movable on the body between an extended position in which the guard obstructs access to the point of the needle and a retracted position in which the guard does not materially obstruct access to the point of the needle, said extended and retracted positions being axially spaced;

means for releasably retaining the guard in the retracted position;

interlocking means on the body and the guard responsive to movement of the guard on the body generally axially to the extended position for interlocking to substantially prevent movement of the guard back toward the retracted position;

an axially extending radially opening channel on said guard and an elongated axially extending rib on said body received in said channel to axially guide the shield between said positions thereof; and said retaining means including a portion of said rib and an interlocking member carried by said channel.

14. An apparatus for injecting a substance into a human or an animal comprising:

a body adapted to have the substance to be injected pass therethrough;

means for mounting a needle on the body with the needle having a passage extending therethrough and terminating in a point whereby the substance can pass from the body to and through the passage of the needle;

a needle guard movable on the body between an extended position in which the guard obstructs access to the point of the needle and a retracted position in which the guard does not materially obstruct access to the point of the needle, said extended and retracted positions being axially spaced;

means for releasably retaining the guard in the retracted position;

interlocking means on the body and the guard responsive to movement of the guard on the body generally axially to the extended position for interlocking to substantially prevent movement of the guard back toward the retracted position;

an axially extending radially opening channel on said guard and an elongated axially extending rib on said body received in said channel to axially guide the shield between said positions thereof; and said interlocking means including a portion of said rib and an interlocking member in said channel and carried by said guard.

* * * * *